United States Patent [19]

Letsinger et al.

[11] Patent Number: 4,547,569
[45] Date of Patent: Oct. 15, 1985

[54] INTERCALATING AGENTS SPECIFYING NUCLEOTIDES

[75] Inventors: Robert L. Letsinger, Evanston, Ill.; Margaret E. Schott, Midland, Mich.

[73] Assignee: The United States of America as represented by the Department of Health and Human Services, Washington, D.C.

[21] Appl. No.: 620,801

[22] Filed: Jun. 14, 1984

Related U.S. Application Data

[63] Continuation-in-part of Ser. No. 444,438, Nov. 24, 1982, abandoned.

[51] Int. Cl.$^4$ ............................................. C07H 19/10
[52] U.S. Cl. ..................................... 536/29; 536/23; 536/27; 536/28
[58] Field of Search ........................ 536/23, 27, 28, 29

[56] References Cited

U.S. PATENT DOCUMENTS 3,440,190  4/1969  Melby .
4,257,774  3/1981  Richardson et al. .
4,321,365  3/1982  Wu et al. .

OTHER PUBLICATIONS

Jacquemin-Sablon, et al., Biochemistry, 18:128, (1979).
Wakelin et al., Biochemistry, 17:5057, (1978).
Capelle et al., Biochemistry, 18:3354, (1979).
LePecq et al., Proc. Natl. Acad. Sci. USA, 72:2915, (1975).
Dervan et al., J. of the Amer. Chem. Soc., 100:1968–1971, (1978).
Migrdichian, Organic Synthesis, vol. 1, p. 367, Reinhold, (1958).

Primary Examiner—Johnnie R. Brown
Assistant Examiner—Elli Peselev
Attorney, Agent, or Firm—John S. Roberts, Jr.

[57] ABSTRACT

This invention discloses a molecule bearing a biologically active group (a phenanthridinium moiety) joined covalently to an oligonucleotide recognition system (a phosphorus nucleoside group) by a linker that permits intercalation of the active group in the pocket formed by the nucleotide and complementary bases in another polynucleotide strand. This class of compounds is illustrated by the following:

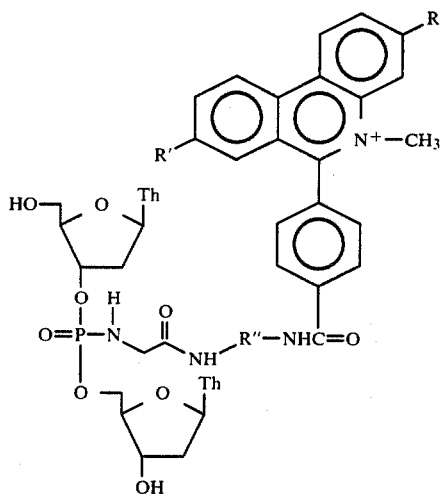

where R is selected from the group consisting of —NH$_2$, methylamino, or ethylamino or hydrogen;
where R' is selected from the group consisting of —NH$_2$, methylamino, or ethylamino or hydrogen;
where the chain linking the linker group to the phenanthridinium group (R'') consists of 2-8 —CH$_2$— groups.

3 Claims, 2 Drawing Figures

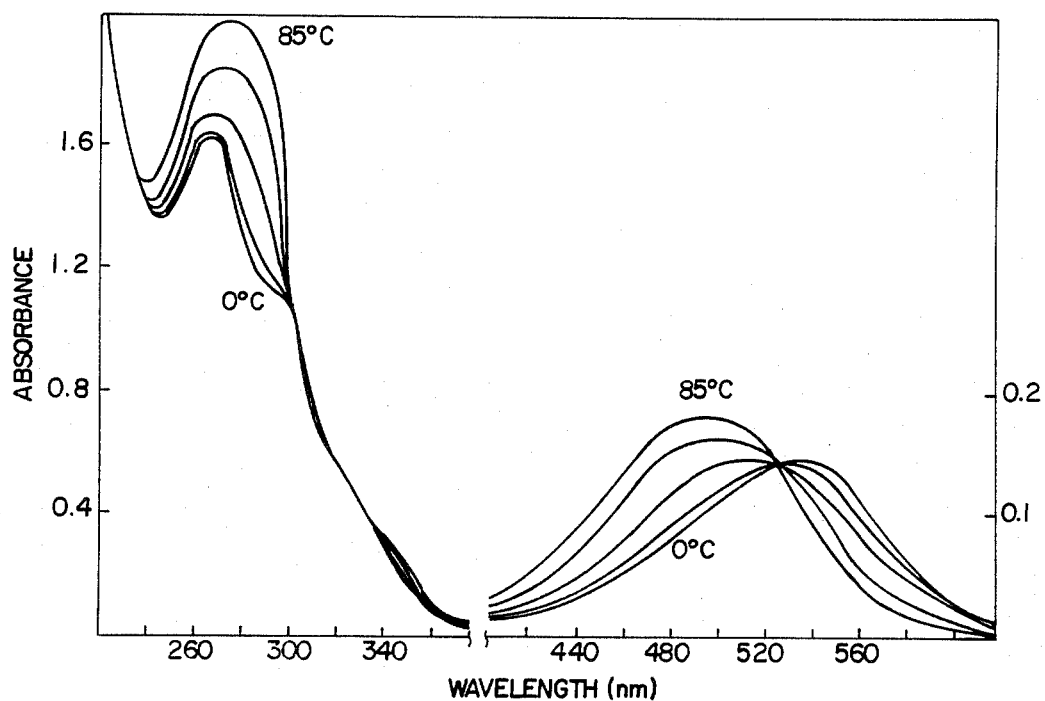
FIG 1
FIG 2
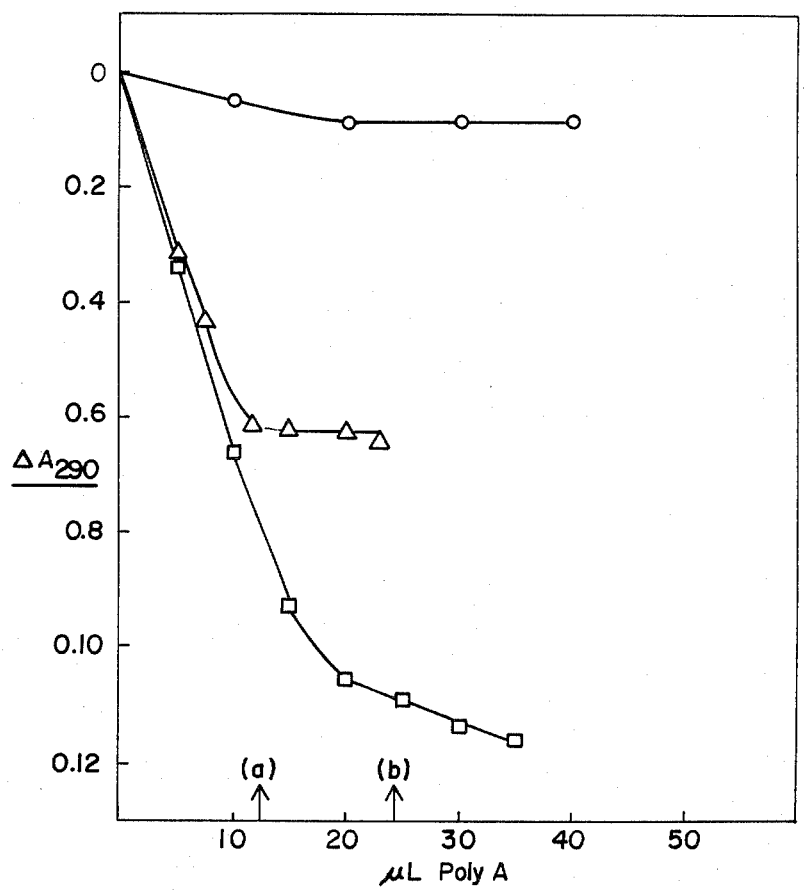

INTERCALATING AGENTS SPECIFYING NUCLEOTIDES

The invention described herein was made in the course of work under a grant or award from the Department of Health and Human Services.

This application is a continuation in part of pending Ser. No. 444,438 filed Nov. 24, 1982, now abandoned.

This invention teaches a molecule bearing a biologically active group (a phenanthridinium moiety) joined covalently to an oligonucleotide recognition system (a phosphorus nucleoside group) by a linker that permits intercalation of the active group in the pocket formed by the nucleotide and complementary bases in another polynucleotide strand.

MATERIAL INFORMATION DISCLOSURE

The publication of this invention appears in the *Journal of the Amer. Chem. Society*, Vol. 103, p. 7394 (1981). Background information may be found in *DNA Replication*, by Arthur Kornberg, published by W. H. Freeman and Company, 1980 (see particularly Chapter 12).

Other articles of interest are:

Jacquemin-Sablon, Helene, et al., *Biochemistry*, Vol. 18, p. 128 (1979).

Wakelin, L. D. G., et al., *Biochemistry*, Vol. 17, p. 5057 (1978).

Capelle, Nicole, et al., *Biochemistry*, Vol. 18, p. 3354 (1979).

LePecq, Jean-Bernard, et. al., *Proc. Natl. Acad. Sci. USA*, Vol. 72, p. 2915 (1975).

Dervan et al., *J. of the Amer. Chem. Soc.*, Vol. 100, pp 1968–71 (1978).

Migrdichian, Vartkes, *Organic Synthesis*, Vol. 1, p. 367, Reinhold Publishing Company (1958).

U.S. Pat. No. 3,440,190 Melby.
U.S. Pat. No. 4,321,365 Wu et al.
U.S. Pat. No. 4,257,774 Richardson et al.

Dervan et al. discloses the formation of one of many phenanthridinium groups. It is, however, different that the present invention in its structure, its formation, and its use. Many phenanthridinium type compounds are known; the phenanthridinium unit described in the present invention is preferred due to the characteristics shown in FIG. 1 and the Example.

Midrdichian discloses the formation of an amide bond, but does not disclose the formation of a bifunctional intercalator.

Melby discloses the preparation of an oligonucleotide, albeit different oligonucleotides than are described in the present invention. As with Dervan et al, the nucleotide of the present invention is preferred due to the characteristics shown in FIG. 1 and the Example.

UTILITY STATEMENT

The compounds of this invention function in standard pharmacological tests on animals as site specific inhibitors for enzymatic processes involving polynucleotides, as reagents for selective cleavage or modification of polynucleotide chains, and as agents for introducing markers (for example, fluorescent probes) at specified regions in polynucleotides. Intercalating agents, well known in the art, are used to inhibit cleavage of DNA strands by restriction endonucleases and can be applied in the analysis of DNA strands. These agents act by inserting themselves (via a mechanism not yet discovered) between two successive nucleotides. In the case of bifunctional intercalaters, of which the present invention are examples, the agent intercalates at two DNA nucleotide sites simultaneously. The presence of a phenanthridium moiety makes these compounds similar in structure and molecular activity to ethidium bromide, the best known intercalater.

DESCRIPTION OF THE FIGURES

FIG. 1 is the absorption spectra of compound 1 (60 µM in dT) and poly A (68 µM in A) in water, 0°–85° C. The left ordinate is for ultraviolet; the right for the visible region.

FIG. 2 is the decrease in absorbance at 290 nm of a solution of ethidium bromide (16 µM), —O—, compound 1 (5 µM), —Δ—, and compound 1 (5 µM) and ethidium bromide (14 µM), —□—, in 925 µL of Tris buffer (0.01 M, pH 6.8) 0.1 M in NaCl on addition of 5 µL increments of an aqueous solution of poly A (380 µM).

BACKGROUND OF THE INVENTION

This invention discloses a class of compounds which can be (a) tailored to bind specifically at any designated oligonucleotide sequence in a polynucleotide, and (b) carry a reactive fragment (an "effector" group) responsive to enzymes or physical probes. These compounds, then, are site specific markers and inhibitors (or initiators) of enzymatic reactions occurring on polynucleotides.

The basic structure of these compounds is:

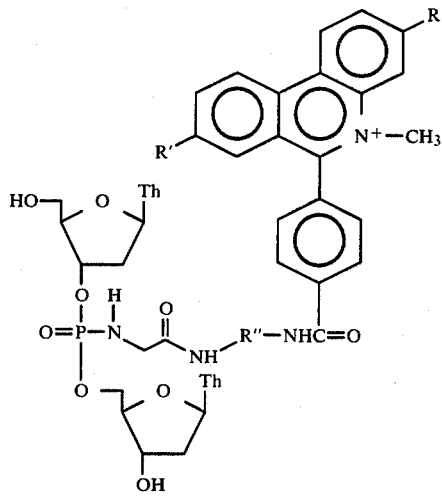

where R is selected from the group consisting of —NH$_2$, methylamino, or ethylamino or hydrogen;

where R' is selected from the group consisting of —NH$_2$, methylamino, or ethylamino or hydrogen;

where the chain linking the linker group to the phenanthridinium group (R") consists of 2-8 —CH$_2$— groups. Ethidium bromide, on the other hand, consists of the structure:

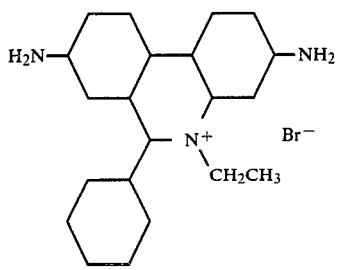

The following represents a presentation of how this class of compounds operates:

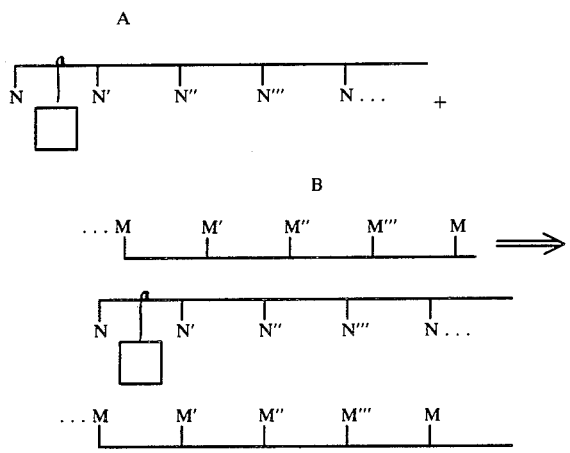

The synthetic target compound "A" contains a sequence of nucleosides, N, N', N" . . . (all four natural deoxyribonucleases are present in the general case), joined by 3'-5' internucleoside links in a backbone that may be negatively charged, electrically neutral, or positively charged. A flat, aromatic molecule (the "effector"), which is also capable of intercalating in DNA, is joined covalently to the backbone by a flexible linker. When compound A encounters a single stranded polynucleotide "B" which has a complementary base sequence (M, M', M" . . . ), a hydrogen bond complex is formed. If the geometry of the linker arm is appropriate, intercalation of the effector into a base pair pocket in the complex occurs, since the effective concentration of this fragment is always high in the vicinity of the complex. In short, compound A is a substance containing a biochemically active fragment bearing a covalently attached recognition system that directs the active fragment to a given nucleotide sequence.

To be effective chemically, the compounds of this invnetion must exhibit certain qualities. Compound A, in the above presentation, must bind to a single stranded polynucleotide more strongly than a natural oligomer does. To be effective in recognizing double stranded DNA—more demanding because compound A must displace and loop out the corresponding strand in the duplex polynucleotide—it is essential that A bind more tightly than the corresponding natural strand.

A number of low molecular weight pharmacologically active compounds bind strongly to polynucleotides. For a review of these compounds, see Patez, D. J., Acc. Chem. Res., Vol. 12, p. 118 (1979). Examples include daunomycin, antinomycin, ellipticenes, the antimalarials chloroquine plus quinacrine, and the antitripanosomal compound ethidium bromide. Some of these exhibit considerable sequence specificity with respect to short segments (for example, actinomycin for d-GC sequences); however, none are specific for an extended oligonucleotide sequence and none have the potential to be made specific for an arbitrarily designated sequence.

Ethidium bromide and the ellipticines are examples of monofunctional intercalators, compounds which intercalate at one DNA site. The chloroquines and the phenanthridines are bifunctional intercalators—binding at two DNA sites simultaneously—rivaling the polymerases and regulatory proteins in their affinity for DNA.

The compounds of this invention exhibit a wide range of uses: (a) DNA, RNA, or protein synthesis could be terminated at a specific nucleotide sequence; (b) single stranded loops susceptible to cleavage by S1 nuclease could be introduced at designated positions in DNA, permitting selective cleavage at any nucleotide sequence (and thus complementing the use of restriction enzymes); and (c) fluorescent labels could be introduced at specific regions of extended polynucleotide chains.

GENERAL DESCRIPTION

The preferred class of compounds of this invention are the phenanthridinium compounds covalently attached to an oligomer of type "A." The diaminophenylphenanthridinium group is particularly attractive for the following reasons: (a) it binds strongly (by intercalation) to double stranded polynucleotides but only weakly to single stranded polynucleotides; (b) it intercalates in all nucleotide pockets in double stranded polynucleotides and is, therefore, sequence specific; (c) linkage through the phenyl group of the phenylphenanthridinium group to an internucleotide phosphorus in the oligomer provides the necessary geometry for interaction; (d) these compounds are soluble in water; (e) these compounds are active biologically (inhibit RNA synthesis in vitro and in vivo, inhibit cell division, and is mutagenic); and (f) these compounds are chemically active (cleave DNA strands upon irradiation in the presence of oxygen). In addition, the compounds of this invention increase the stability of the complex, similar to the pharmacologically active intercalators mentioned in the previous section. When any of these substances bind to DNA, the temperature of dissociation of the two polynucleotide strands ($T_m$) increases.

As previously stated, these compounds are the synthesis products containing (a) a modified oligonucleotide chain (recognition region) and (b) a covalently attached group capable of interacting with DNA (the "effector" unit). The preferred compound contains an effector unit of diaminomethylphenylphenanthridinium covalently linked to a recognition region of thymidylylthymidine:

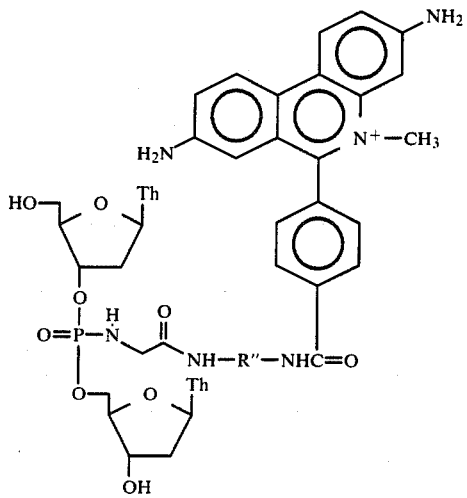

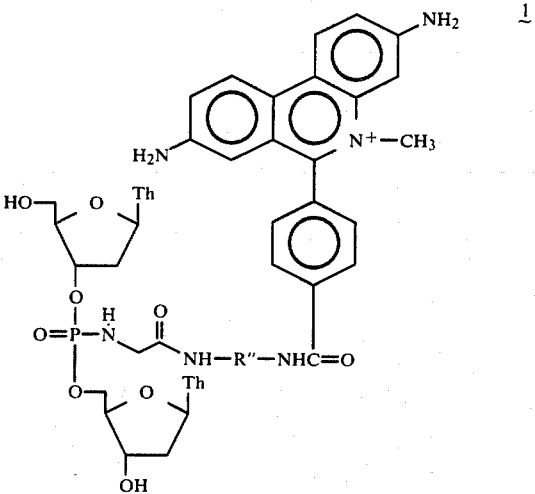

SPECIFIC DESCRIPTION OF THE INVENTION

Compound 1 was synthesized as a prototype of a molecule bearing a biologically active group (diaminomethylphenylphenanthridinium) joined covalently to an oligonucleotide recognition system (thymidylylthymidine) by a linker that permits intercalation of the active group in the pocket formed by the nucleotide and complementary bases in another polynucleotide strand. Spectrophotometric data show that 1 binds strongly to poly A at 0° C. and weakly or not at all with poly G, poly C, poly U and poly I. On warming, the complex with poly A dissociates ($T_m \sim 47°$ C. in absence of salt, $\sim 25°$ C. in 0.1M NaCl). The strong interaction of 1 with poly A is attributed to the presence of two types of binding sites in 1 which can act cooperatively, the phenanthridinium ring and the pyrimidine bases (which show Watson-Crick type selectivity).

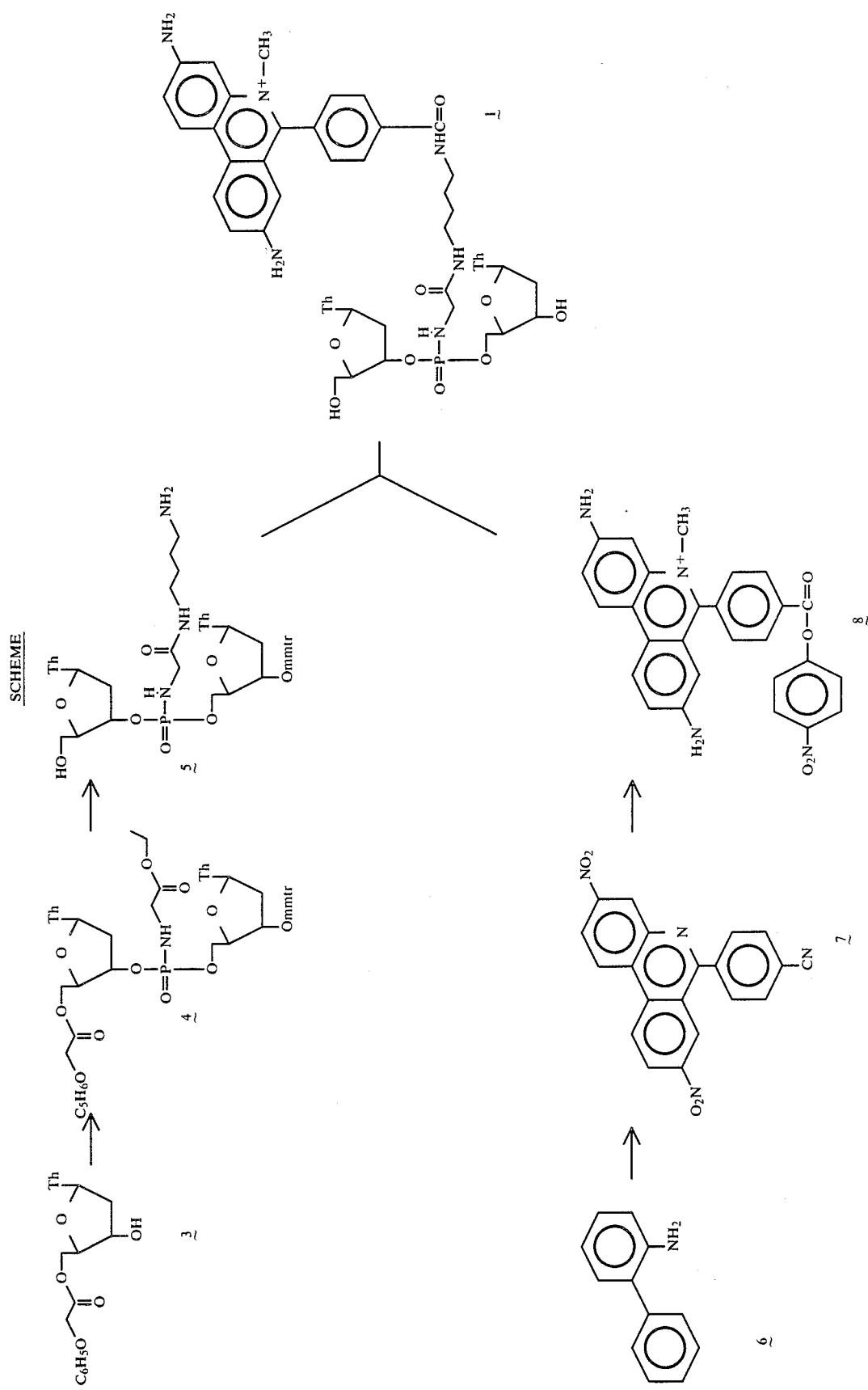

As outlined in the scheme, compound 1 was obtained by constructing the nucleotide portion (5) and the phenanthridinium unit (i) and then linking these two fragments via an amide bond. For synthesis of 5, 2-chlorophenyl phosphorodichloridite (0.9 eq.) in THF:$C_5H_5N$ (2/1) was treated successively with triazole (3 eq., 5 min), 5'-0-phenoxyacetylthymidine (1 eq., −78° C., 20 min) and 3'-0-di-p-methoxytritylthymidine (0.5 eq., −78° to 0° C., 30 min.). The resulting phosphite was converted without isolation to phosphoramidate 4 by reaction with excess ethyl azidoacetate and water in THF (room temp., 40 h), and 4 was converted to 5 by treatment with excess 1,4-diaminobutane in dioxane (40° C., 40 h).

The phenanthridinium unit was prepared from 2-aminobiphenyl by adaptation of reported procedures [Dervan, P. B., and Becker, M. M., *J. Am. Chem. Soc.*, Vol. 100, p. 1968 (1978); and Kuhlmann, K. F., Charbeneau, N. J., and Mosher, C. W., *Nucleic Acids Res.*, Vol. 5, p. 2629 (1978)]. Nitration ($H_2SO_4$ and $KNO_3$, 5° C., 4 h), aroylation with 4-cyanobenzoyl chloride (90 min in refluxing $C_6H_5Cl$), and cyclization ($POCl_3$, 2 h in refluxing $C_6H_5NO_2$) gave phenanthridine 7. Methylation ($Me_2SO_4$, 180° C. in $C_6H_5NO_2$ for 1 h), hydrolysis of the nitrile (75% aq. $H_2SO_4$, 130° C., 90 min), reduction of the nitro groups (Fe:48% HBr, 3 h at reflux) and esterification with nitrophenol (DCC in DMF:$C_5H_5N$ (3/1), 6 h) yielded the active ester (8). Compound 1 was then obtained by reaction of equimolar amounts of 5 and 8 in DMF followed by detritylation with 80% aq. acetic acid (4 h).

The interaction of 1 with polyadenylate (poly A) in aqueous solution was examined spectrophotometrically. In dilute solution, ethidium bromide, a closely related phenanthridinium compound, exhibits a strong bathochromic shift ($\lambda_{max}$ 478→518 nm) and a reduction in intensity of the visible absorption band on binding to duplex polynucleotides. As shown in FIG. 1, compound 1 exhibits a similar shift in the presence of single stranded poly A ($\lambda_{max}$ 495→534 nm at 0° C.). With an increase in temperature from 0° to 85° C. the complex "melts out" over a rather broad range and the maximum returns to 497 nm. The midpoint of the transition, $T_m$, is near 47° C. as determined in either the visible (490 nm) or ultraviolet (280 nm) region and is relatively high ($T_m$ 25° C.) even for solutions 0.1M in NaCl. For comparison, thymidine oligonucleotides smaller than the pentamer fail to bind to poly A at 0° C., and neither of the neutral triester derivatives, $dT_{Et}T$ or $dT_{Me}T_{Me}T_{Me}T$, react with poly A at comparable concentrations.

Titration of a solution of 1 in 0.1M NaCl with poly A indicated formation of a complex with a ratio of phenanthridinium (in 1) to phosphorus (in poly A) close to one (middle curve, FIG. 2). Although very little ethidium binds directly to poly A (top curve, FIG. 2), an interaction of ethidium with the complex of poly A and 1 was observed (bottom curve, FIG. 2). These data are consistent with a model for the complexes formed with limited poly A in which molecules of 1 are aligned along the poly A chain with additional phenanthridinium moieties (from a second equivalent of 1 or from added ethidium) interspersed between them.

EXAMPLE

An oligonucleotide derivative possessing a structural feature that enhances binding of the oligomer to complementary sequences in a polynucleotide has interest as a site specific inhibitor (or promoter) of enzymatic processes involving the polynucleotide. Experiments show that the model compound in the scheme is capable of intercalating in the base pair pockets of DNA.

Compound 1 was selected because the "melting temperature," $T_m$, of a double stranded polynucleotide is increased when ethidium or related substances intercalate, that ethidium intercalates even in dinucleotide pockets at sufficiently high concentrations, and that an intercalator with two binding sites (i.e., a bis-intercalator) forms a much tighter complex with DNA than one with a single binding site (a mono-intercalator). Molecular models indicate that the linker arm in 1 should permit the phenanthridinium moiety to fold back and insert into the pocket formed by the adjoined nucleoside bases and the complementary bases in a polynucleotide. In effect, the local concentration of the ethidium-like group is always high in the vicinity of the dinucleotide. Compound 1 is therefore representative of an oligonucleotide derivative with two types of binding sites that act cooperatively, the phenanthridinium ring and the pyrimidine bases. Alternatively, Compound 1 is of interest as a model for a biologically active substance (the diaminophenanthridinium ring) with a covalently attached recognition system that directs the active agent to a given nucleotide sequence.

As outlined in the scheme, Compound 1 was obtained by constructing the nucleotide portion (5) and the phenanthridinium unit (8) and then linking these two fragments via an amide bond. For synthesis of 5, 2-chlorophenyl phosphorodichloridite (0.9 eq.) in THF:$C_5H_5N$ (2/1) was treated successively with triazole (3 eq., 5 min), 5'-0-phenoxyacetylthymidine (1 eq., −78° C., 20 min) and 3'-O-di-p-methoxytritylthymidine (0.5 eq., −78° to 0° C., 30 min). The resulting phosphite was converted without isolation to phosphoramidate 4, by reaction with excess ethyl azidoacetate and water in THF (room temp., 40 h), and 4 was converted to 5 by treatment with excess 1,4-diaminobutane in dioxane (40° C., 40 h). The phenanthridinium unit (8) was prepared from 2-aminobiphenyl by adaptation of reported procedures (Dervan, cited above). Nitration ($H_2SO_4$ and $KNO_3$, 5° C., 4 h), aroylation with 4-cyanobenzoyl chloride (90 min in refluxing $C_6H_5Cl$), and cyclization ($POCl_3$, 2 h in refluxing $C_6H_5NO_2$) gave phenanthridine 7. Methylation ($Me_2SO_4$, 180° C. in $C_6H_5NO_2$ for 1 h), hydrolysis of the nitrile (75% aq. $H_2SO_4$, 130° C., 90 min), reduction of the nitro groups (Fe:48% HBr, 3 h at reflux) and esterification with nitrophenol (DCC in DMF:$C_5H_5N$ (3/1), 6 h) yielded the active ester (8). Compound 1 was then obtained by reaction of equimolar amounts of 5 and 8 in DMF followed by detritylation with 80% aq. acetic acid (4 h).

The interaction of 1 with polyadenylate (poly A) in aqueous solution was examined spectrophotometrically. In dilute solution, ethidium bromide, a closely related phenanthridinium compound, exhibits a strong bathochromic shift ($\lambda_{max}$ 478→518 nm) and a reduction in intensity of the visible absorption band on binding to duplex plynucleotides. As shown in FIG. 1, comound 1 exhibits a similar shift in the presence of single stranded poly A ($\lambda_{max}$ 495→534 nm at 0° C.). With an increase in temperature from 0° to 85° C. the complex "melts out" over a rather broad range and the maximum returns to 497 nm. The midpoint of the transition, $T_m$, is near 47° C. as determined in either the visible (490 nm) or ultraviolet (280 nm) region and is relatively high ($T_m$ 25° C.) even for solutions 0.1M in NaCl. For comparison, thymidine oligonucleotides smaller than the pentamer fail to bind to poly A at 0° C., and neither of the neutral triester derivatives, $dT_{Et}T$ or $dT_{Me}T_{Me}T_{Me}T$, react with poly A at comparable concentrations.

Titration of a solution of 1 in 0.1M NaCl with poly A indicated formation of a complex with a ratio of phenanthridinium (in 1) to phosphorus (in poly A) close to one (middle curve, FIG. 2). Although very little ethidium binds directly to poly A (top curve, FIG. 2), an interaction of ethidium with the complex of poly A and 1 was observed (bottom curve, FIG. 2). These data are consistent with a model for the complexes formed with limited poly A in which molecules of 1 are aligned along the poly A chain (as in Compound 2) with additional phenanthridinium moieties (from a second equivalent of Compound 1 or from added ethidium) interspersed between them.

In control experiments it was found that addition of the ethyl ester of thymidylyl-(3'-5')-thymidine ($dT_{Et}T$) (60 μM) has no effect on the spectrum of ethidium bromide (30 μM) in a solution of poly A (60 μM) at 0° C., either in the presence or absence of NaCl (0.1M). Furthermore, spectral data show little or no interaction of 1 with poly G, poly C, and poly U. The spectral shifts exhibited on addition of poly A to aqueous solutions of 1 demonstrate formation of a complex stabilized both by specific Watson-Crick base pairing and by an interaction involving a phenanthridinium group favorably positioned by covalent attachment to the thymidine nucleotide.

While the invention has been described in connection with specific embodiments, it should be understood that the invention is capable of further modifications and this application is intended to cover any variations, uses, or adaptations. For example, the compound described above contains two phosphorus nucleosides—up to twenty may be used to produce even greater sequence specificity. Such a compound is illustrated below:

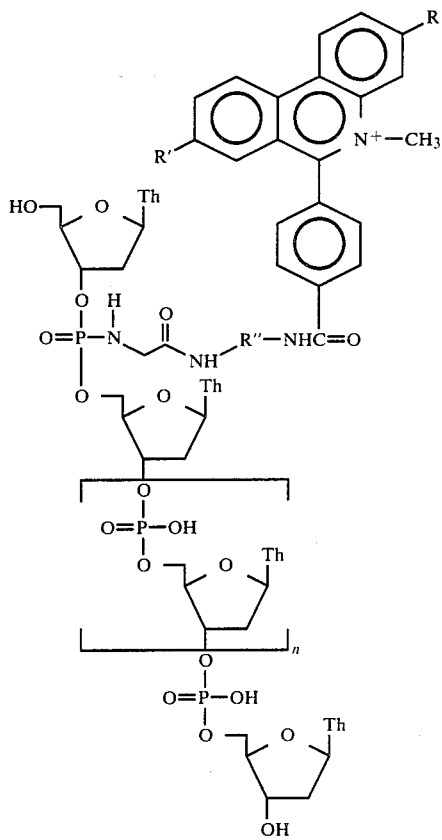

wherein R, R', and R" are previously defined; and n is an integer from 0 to 19. These nucleosides are bonded using conventional techniques.

In addition, the length of the linker chain (the chain that links the phosphorus nucleosides to the phenanthridinium group) may be extended to include up to eight additional —$CH_2$— groups or reduced to two. Another alternative is the methylamino or ethylamino or hydrogen substitution of the amino group on the phenanthridinium ring. Acid addition salts and amino salts of organic and inorganic acids are included within the scope of this invention.

We claim:

1. The compound of the formula

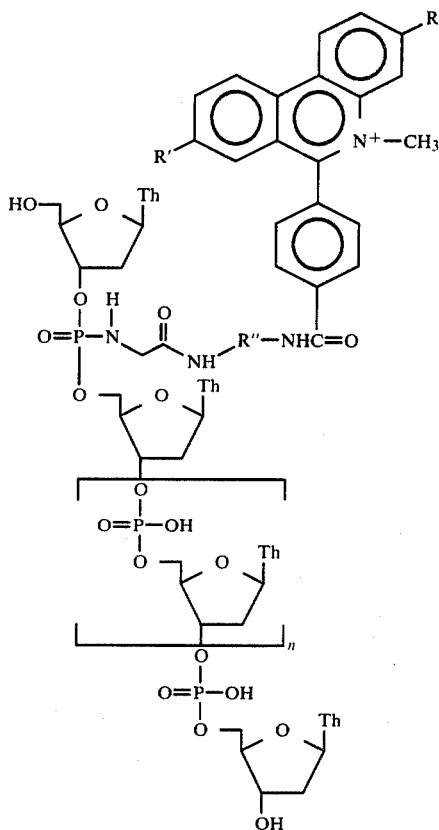

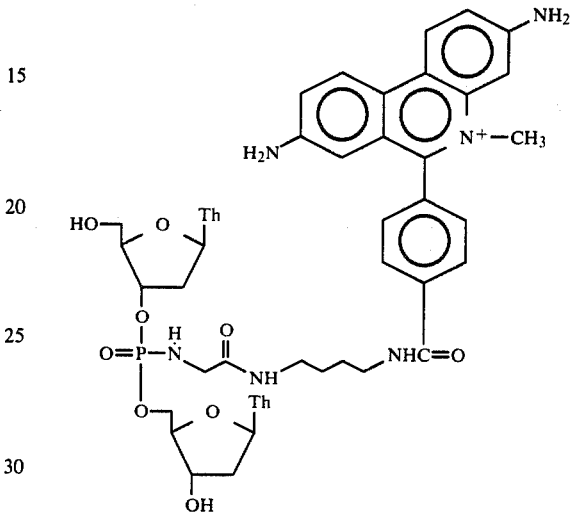

where R is selected from the group consisting of —NH$_2$, methylamino, or ethylamino or hydrogen;
where R' is selected from the group consisting of —NH$_2$, methylamino, or ethylamino or hydrogen;
where the chain linking the linker group to the phenanthridinium group (R") consists of 2-8 —CH$_2$— groups;
where Th is thymidylyl thymidine; and
where n is an integer from 0-19.

2. The compound of the formula:

where Th is thymidylyl thymidine.

3. The compound of claim 1 which consists of 2 phosphorus nucleosides.

* * * * *